US009650408B2

(12) United States Patent
Tsuruta

(10) Patent No.: US 9,650,408 B2
(45) Date of Patent: May 16, 2017

(54) THERAPEUTIC AGENT FOR HYPERTENSION

(75) Inventor: Hideo Tsuruta, Chiyoda-ku (JP)

(73) Assignee: SRI INTERNATIONAL, Menlo park, CA (US)

( * ) Notice: Subject to any disclaimer, the term of this patent is extended or adjusted under 35 U.S.C. 154(b) by 1850 days.

(21) Appl. No.: 12/064,677

(22) PCT Filed: Aug. 28, 2006

(86) PCT No.: PCT/JP2006/316878
§ 371 (c)(1),
(2), (4) Date: Feb. 25, 2008

(87) PCT Pub. No.: WO2007/026651
PCT Pub. Date: Mar. 8, 2007

(65) Prior Publication Data
US 2009/0281071 A1 Nov. 12, 2009

(30) Foreign Application Priority Data
Aug. 29, 2005 (JP) .................. 2005 248212

(51) Int. Cl.
A61K 31/56 (2006.01)
A61K 31/573 (2006.01)
C07J 5/00 (2006.01)

(52) U.S. Cl.
CPC .............. C07J 5/00 (2013.01); A61K 31/573 (2013.01)

(58) Field of Classification Search
USPC ........................................ 514/183
See application file for complete search history.

(56) References Cited

U.S. PATENT DOCUMENTS

| 5,447,941 A | 9/1995 | Zuckerman |
| 6,503,896 B1 | 1/2003 | Tanabe et al. |
| 2002/0032180 A1 | 3/2002 | Tanabe et al. |

FOREIGN PATENT DOCUMENTS

| GB | 2 374 412 A | 10/2002 |
| WO | WO 99/33859 | 7/1999 |
| WO | WO 00/33828 | 6/2000 |
| WO | WO 01/26651 A2 | 4/2001 |

OTHER PUBLICATIONS

Blakely et al., A Phase I and Pharmacokinetic Study of TAS-108 in Postmenopausal female patients with locally advanced, locally recurrent inoperable, or progressive metastatic breast cancer, 2004, Clinical Cancer Research, vol. 10, pp. 5425-5431.*
Thorin et al., Hyper-reactivity of cerebral arteries from ovariectomized rats: therapeutic benefit of tamoxifen, 2003, British Journal of Pharmacology, vol. 140, pp. 1187-1192.*
Tsuda et al., A selective estrogen receptor modulator, tamoxifen, and membrane fluidity of erythrocytes in normotensive and hypertensive postmenopausal women: An electron Paramagnetic Resonance Investigation, 2005, American Journal of Hypertension, vol. 18 (8), pp. 1067-1076, Abstract Only.*
Oparil, Hypertension in postmenopausal women: pathophysiology and management, 1995, Curr Opin Neophrol Hypertens, 4 (5), 438-442, Abstract Only.*
Wassmann et al., Raloxifene improves endothelial dysfunction in hypertension by reduced oxidative stress and enhanced nitric oxide production, 2002, Circulation, vol. 105, pp. 2083-2091.*
Brosnihan et al., Effects of droloxifene, a new selective estrogen receptor modulator (SERM), on blood pressure and the renin-angiotensin system in healthy post-menopausal women, 2000, J. Am. Coll. Cardiol., vol. 35, No. 2, Suppl. A, 225A, Abstract Only.*
Gonzalez-Perez et al.,Toremifene improves vascular function in menopause-induced rats, 2003, FASEB Journal, vol. 17, No. 4-5, Abstract No. 75.21, Abstract Only.*
"EPO Examination Guidelines", http://www.epo.org/law-practice/legal-texts/html/guidelines/e/g_ii_4_2.htm, accessed Oct. 2, 2014, one page.*
Da Costa, Lilian et al., "Effects of Hormone Replacement Therapy of Raloxifene on Ambulatory Blood Pressure and Arterial Stiffness in Treated Hypertensive Postmenopausal Women", The American Journal of Cardiology, vol. 94, No. 11, pp. 1453 to 1456, 2004.
"1999 World Health Organization-International Society of Hypertension Guidelines for the Management of Hypertension", Journal of Hypertension, Guidelines Subcommittee, vol. 17, No. 2, 1999, pp. 151-183.
"Endocrinology: Molecular and Preclinical 2", Proceedings of the American Association for Cancer Research Annual Meeting, vol. 42, Mar. 2001, p. 270.

* cited by examiner

Primary Examiner — Jeffrey S Lundgren
Assistant Examiner — Meghan Finn
(74) Attorney, Agent, or Firm — Richard Aron Osman

(57) ABSTRACT

The present invention provides a novel hypertension therapeutic agent.
The hypertension therapeutic agent of the present invention contains, as an active ingredient, a compound represented by formula (1):
[F1]

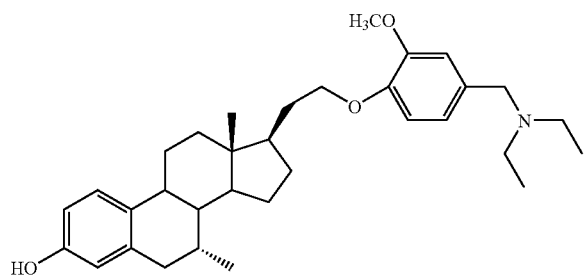

(1)

or a pharmaceutically acceptable salt thereof.

20 Claims, 4 Drawing Sheets

THERAPEUTIC AGENT FOR HYPERTENSION

TECHNICAL FIELD

The present invention relates to a therapeutic agent for hypertension (hereinafter may be referred to as a "hypertension therapeutic agent"), and to an agent for alleviating hypertension in postmenopausal breast cancer patients.

BACKGROUND ART

Hypertension refers to an excessive increase in either of the following blood pressures: systolic blood pressure; i.e., maximum blood pressure as measured when the heart contracts to pump blood into arteries; and diastolic blood pressure; i.e., minimum blood pressure as measured when the heart is dilated and filled with blood. According to the World Health Organization (WHO), hypertension is defined as a maximum blood pressure (a systolic blood pressure) of higher than 140 mmHg, or a minimum blood pressure (a diastolic blood pressure) of higher than 90 mmHg (Non-Patent Document 1). Hypertension is classified into two types: essential hypertension, which cannot be attributed to any particular cause, and secondary hypertension, resulting from an apparent cause. Essential hypertension has been reported to account for 90% or more of all hypertensive cases. Essential hypertension, which often develops after middle age and becomes chronic, is a leading cause of death worldwide, since it is a condition of high prevalence, causes damage to major organs (e.g., the brain, the heart, and the kidneys), and closely relates the course of other arteriosclerotic diseases.

Generally employed hypertension therapeutic agents include (1) a calcium antagonist, (2) an angiotensin-converting enzyme inhibitor, (3) an angiotensin II receptor antagonist, (4) a diuretic, and (5) a sympatholytic agent. However, each of these hypertension therapeutic agents exhibits side effects, and may fail to be administered to some patients. Therefore, demand has arisen for a hypertension therapeutic agent based on a new mechanism.

(7α)-21-[4-[(Diethylamino)methyl]-2-methoxyphenoxy]-7-methyl-19-norpregna-1,3,5(10)-trien-3-ol or a pharmaceutically acceptable salt thereof (see the following structural formula (1), a citric acid salt of the compound may be abbreviated as "TAS-108") has strong affinity to estrogen receptor (ER), and is known as an excellent breast cancer therapeutic agent (Patent Document 1 and Non-Patent Document 2).

[F1]

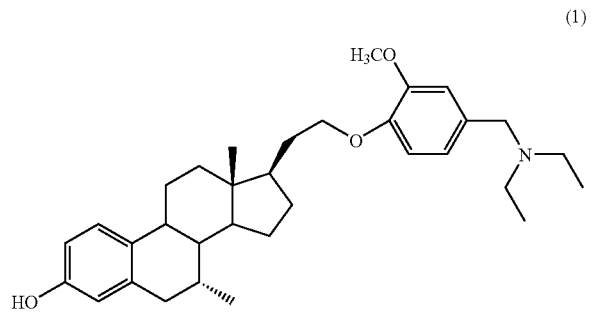 [SMILES: CCN(CC)Cc1ccc(OCC[C@H]2CCC3C4C(CC[C@@]32C)c2ccc(O)cc2C[C@H]4C)c(OC)c1]

(1)

This compound is also considered useful as a therapeutic agent for pulmonary hypertension or osteoporosis (see, for example, Patent Document 1). Pulmonary hypertension is a disease in which it is difficult for blood to pass through narrowed peripheral arteriolar lumens of blood vessels carrying blood from the heart to the lungs (i.e., pulmonary arteries), resulting in an increase in blood pressure in the pulmonary arteries (pulmonary arterial pressure). Since the right ventricle of the heart, which pumps blood into the pulmonary arteries, cannot endure high pressure, continuously high pulmonary arterial pressure causes deterioration in right ventricular function, leading to right ventricular failure. In general, normal pulmonary arterial pressure is 30 to 15 mmHg (systolic), 8 to 2 mmHg (diastolic), and 18 to 9 mmHg (mean). Therefore, pulmonary hypertension is defined as a systolic pulmonary arterial pressure of 30 mmHg or higher, or a mean pulmonary arterial pressure of 20 mmHg or higher. According to statistics compiled by the Japanese Ministry of Health, Labor and Welfare in 2003, in Japan, the number of patients with primary pulmonary hypertension (see classification of pulmonary hypertension) has been increasing year by year, and was reported to be 637 in 2002. Unlike the case of systemic hypertension, pulmonary hypertension is often complicated with various cardiopulmonary diseases. Pulmonary hypertension which is not associated with such diseases is called primary pulmonary hypertension (PPH), and is designated as a specified disease (i.e., an intractable disease). Thus, pulmonary hypertension completely differs from systemic hypertension in terms of symptoms and definition.

Selective estrogen receptor modulators (SERMs) are a class of chemically synthesized drugs which bind to estrogen receptor α (ERα), and which exhibit both estrogenic (agonistic) effect and anti-estrogenic (antagonistic) effect in an organ-specific manner. Tamoxifen and raloxifene, which are typical SERMs, exhibit agonistic effect on bone tissue and lipid metabolism, and antagonistic effect on mammary tissue. It has been reported that these SERMs can be used for blood pressure control (Patent Documents 2 to 4). However, actual tests have shown that when raloxifene, which is a typical SERM, is administered to postmenopausal hypertensive patients, a systolic blood pressure of 142±13 mmHg is reduced only to 139±10 mmHg (Non-Patent Document 3).

Patent Document 1: WO 99/33859
Patent Document 2: GB Patent No. 2374412
Patent Document 3: WO 2001/26651
Patent Document 4: JP-A-2002-531496
Non-Patent Document 1: J. Hypertens., 1999; 17: 151-183
Non-Patent Document 2: Proceedings of the American Association for Cancer Research Annual Meeting, (March, 2001) Vol. 42, pp. 270
Non-Patent Document 3: Am. J. Cardiol., 2004; 94: 1453-1456

DISCLOSURE OF THE INVENTION

Problems to be Solved by the Invention

An object of the present invention is to provide a hypertension therapeutic agent based on a new mechanism, which agent exhibits excellent hypotensive effect in hypertensive patients, and does not affect normotensive patients.

Means for Solving the Problems

The present inventor has studied on the therapeutic effect, on hypertension, of TAS-108, which exhibits virtually no agonistic effect on estrogen receptor α but exhibits potent antagonistic effect thereon, and as a result has found that, quite unexpectedly, TAS-108 very considerably reduces the blood pressure of postmenopausal hypertensive patients on whom conventional SERMs exhibit virtually no hypotensive effect, and barely reduces the blood pressure of normotensive patients. The present invention has been accomplished on the basis of this finding.

Accordingly, the present invention provides a hypertension therapeutic agent containing, as an active ingredient, (7α)-21-[4-[(diethylamino)methyl]-2-methoxyphenoxy]-7-methyl-19-norpregna-1,3,5(10)-trien-3-ol represented by the following formula (1):
[F2]

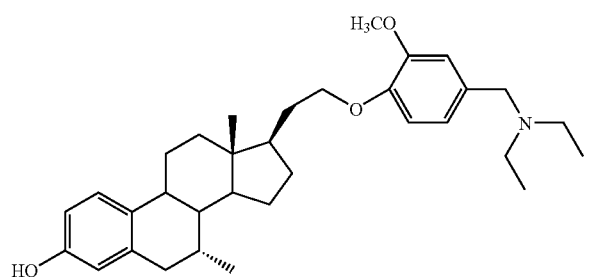

(1)

or a pharmaceutically acceptable salt thereof.

The present invention also provides an agent for alleviating hypertension (hereinafter may be referred to as a "hypertension-alleviating agent") in a postmenopausal breast cancer patient, the agent containing, as an active ingredient, the compound represented by formula (1) or a pharmaceutically acceptable salt thereof.

The present invention also provides a method for the treatment of hypertension, or a method for alleviating hypertension in a postmenopausal breast cancer patient, characterized in that the method comprises administering the compound represented by formula (1) or a pharmaceutically acceptable salt thereof to a subject in need thereof.

The present invention also provides use of the compound represented by formula (1) or a pharmaceutically acceptable salt thereof for producing a hypertension therapeutic agent or an agent for alleviating hypertension in a postmenopausal breast cancer patient.

Effects of the Invention

The hypertension therapeutic agent of the present invention exhibits significant effect of reducing a high systolic blood pressure of 140 mmHg or higher to a normal level. In addition, the hypertension therapeutic agent can reduce the blood pressure of a patient with a diastolic blood pressure of higher than 90 mmHg to a normal level. Meanwhile, the hypertension therapeutic agent barely reduces the blood pressure of a patient with a systolic blood pressure of 140 mmHg or lower. Such a hypotensive effect is particularly pronounced in postmenopausal women; in particular, postmenopausal breast cancer patients.

BEST MODES FOR CARRYING OUT THE INVENTION

Figure 1:
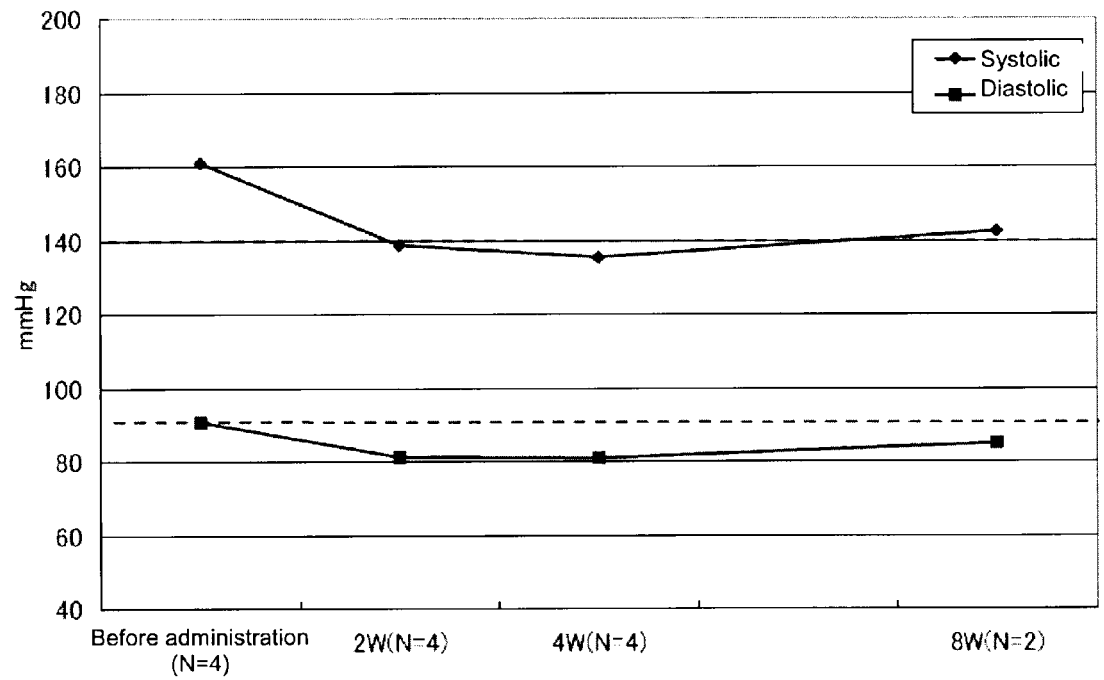
FIG. 1 shows changes in mean blood pressure of four hypertensive patients with a systolic blood pressure of 140 mmHg or higher.

The compound represented by formula (1) or a pharmaceutically acceptable salt thereof, which is employed in the present invention, may be produced through, for example, a method described in Patent Document 1.

No particular limitation is imposed on the pharmaceutically acceptable salt of the compound employed in the present invention, so long as the salt is a conventionally known one. The pharmaceutically acceptable salt is preferably an acid addition salt. Examples of acids suitable for preparing the acid addition salt include organic acids such as acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluenesulfonic acid, and salicylic acid; and inorganic acids such as hydrochloric acid, hydrobromic acid, sulfuric acid, nitric acid, and phosphoric acid. Among them, organic acids are preferred, with citric acid being more preferred. Notably, a citric acid salt of the compound will be referred to as "TAS-108."

As described in the Examples hereinbelow, the compound represented by formula (1) or a pharmaceutically acceptable salt thereof exhibits the effect of reducing the blood pressure of a hypertensive patient with a systolic blood pressure of 140 mmHg or higher to a normal systolic pressure of lower than 140 mmHg. In addition, the compound or a pharmaceutically acceptable salt thereof exhibits the effect of reducing the blood pressure of a patient with a diastolic blood pressure of higher than 90 mmHg to a normal diastolic pressure of lower than 90 mmHg. Meanwhile, the compound or a pharmaceutically acceptable salt thereof does not reduce the blood pressure of a patient with a normal systolic blood pressure of lower than 140 mmHg. Such a hypotensive effect is maintained for a long period of time. Therefore, the pharmaceutical agent of the present invention is useful as a therapeutic agent for systemic hypertension (e.g., essential hypertension).

The hypertension therapeutic agent of the present invention is intended to be administered to patients with systemic hypertension. The therapeutic agent is preferably intended to be administered to patients with essential hypertension, and more preferably to postmenopausal women (in particular, postmenopausal breast cancer patients).

As has been known, the QOL of breast cancer patients is often unsatisfactory. For example, risk of associated diseases increases after menopause (e.g., manifestations of hypertension due to an increase in blood pressure, hyperlipidemia due to an increase in blood cholesterol level, and osteoporosis due to a decrease in bone density) (see Treat Endocrinol. 2004; 3 (5): 289-307). The pharmaceutical agent of the present invention is also employed as a hypertension-alleviating agent for alleviating hypertension (i.e., a risk factor) in postmenopausal breast cancer patients. The pharmaceutical agent of the present invention is useful, since, when the pharmaceutical agent is administered to a breast cancer patient before or after menopause, the systolic blood pressure is maintained at a normal level of lower than 140 mmHg, and the diastolic blood pressure is maintained at a normal level of lower than 90 mmHg.

The pharmaceutical agent of the present invention may be prepared into a variety of dosage forms. Such dosage forms may be, for example, peroral agents, injections, rectal suppositories, or external preparations (e.g., ointments or patches), which can be produced through conventional formulation methods known to those skilled in the art. A peroral solid product (e.g., tablets, coated tablets, granules, powder, or capsules) can be prepared by adding, to the active ingredient, an excipient and, if necessary, an additive such as a binder, a disintegrating agent, a lubricant, a coloring agent, a sweetening agent, or a flavoring agent, followed by customary processing. A peroral liquid product (e.g., an oral solution or a syrup) can be prepared by adding, to the active ingredient, an additive such as a sweetening agent, a buffer, a stabilizer, or a flavoring agent, followed by customary processing. An injection (a subcutaneous injection, an intramuscular injection, or an intravenous injection) can be prepared by adding, to the active ingredient, a pH-adjusting agent, a buffer, a stabilizer, a tonicity agent, a local anesthetic agent, or the like, followed by customary processing. A rectal suppository can be prepared by adding, to the active ingredient, an excipient and, if necessary, an additive such as a surfactant, followed by customary processing. An ointment (in the form of, for example, paste, cream, or gel) is formulated by mixing, through a customary technique, the active ingredient with, if necessary, a generally employed additive such as a base, a stabilizer, a humectant, or a preservative. Examples of the base which may be employed include white petrolatum, paraffin, glycerin, a cellulose derivative, polyethylene glycol, silicone, and bentonite. Examples of the preservative which may be employed include methyl p-hydroxybenzoate, ethyl p-hydroxybenzoate, and propyl p-hydroxybenzoate. A patch can be prepared by applying, to a generally employed support, the aforementioned ointment, cream, gel, or paste, or the like through a customary technique. Examples of appropriate supports include woven fabrics and non-woven fabrics made of cotton, staple fiber, and chemical fiber; and films and foam sheets made of soft vinyl chloride, polyethylene, and polyurethane.

The amount of the compound represented by formula (1) or a pharmaceutically acceptable salt thereof incorporated into any of the aforementioned product forms per unit dose varies with, for example, the symptom of a patient in need thereof, or the product form. In general, preferably, the amount of the compound or a pharmaceutically acceptable salt thereof per unit dose is about 5 to about 1,000 mg (for a peroral agent), about 0.1 to about 500 mg (for an injection), and about 5 to about 1,000 mg (for a suppository or an external preparation).

The daily dose of the compound represented by formula (1) or a pharmaceutically acceptable salt thereof which is in any of the aforementioned dosage forms varies depending on the symptom, etc. of a patient in need thereof and cannot be unequivocally determined. However, in general, the daily dose is preferably about 0.1 to about 5,000 mg.

EXAMPLES

The present invention will next be described in more detail with reference to Formulation Examples and Examples. However, the present invention is not limited to these Examples.

Formulation Example 1 Tablets

| | |
|---|---|
| TAS-108 | 50 mg |
| Cornstarch | 50 mg |
| Microcrystalline cellulose | 50 mg |
| Hydroxypropyl cellulose | 15 mg |
| Lactose | 47 mg |
| Talc | 2 mg |
| Magnesium stearate | 2 mg |
| Ethyl cellulose | 30 mg |
| Unsaturated glyceride | 2 mg |
| Titanium dioxide | 2 mg |

Tablets (250 mg per tablet) having the aforementioned formulation were prepared through a customary method.

Formulation Example 2 Granules

| | |
|---|---|
| TAS-108 | 300 mg |
| Lactose | 540 mg |
| Cornstarch | 100 mg |
| Hydroxypropyl cellulose | 50 mg |
| Talc | 10 mg |

Granules (1,000 mg per package) having the aforementioned formulation were prepared through a customary method.

Formulation Example 3 Capsules

| | |
|---|---|
| TAS-108 | 100 mg |
| Lactose | 30 mg |
| Cornstarch | 50 mg |
| Microcrystalline cellulose | 10 mg |
| Magnesium stearate | 3 mg |

Capsules (193 mg per capsule) having the aforementioned formulation were prepared through a customary method.

Formulation Example 4 Injection

| | |
|---|---|
| TAS-108 | 100 mg |
| Sodium chloride | 3.5 mg |
| Distilled water for injection | Appropriate amount (2 mL per ampule) |

An injection having the aforementioned formulation was prepared through a customary method.

Formulation Example 5 Suppositories

| | |
|---|---|
| TAS-108 | 300 mg |
| Witepsol W-35 (registered trademark, mixture of mono-, di-, and triglycerides of saturated fatty acids (lauric acid to stearic acid), product of Dynamite Nobel) | 1,400 mg |

Suppositories having the aforementioned formulation were prepared through a customary method.

Example 1

<Method>

TAS-108 (40 mg, 80 mg, or 120 mg) was orally administered to postmenopausal breast cancer patients (age: 50 to 78) once a day after breakfast for up to eight weeks. Blood pressure was measured in a sitting position before administration on the day of initiation of administration, and two weeks, four weeks, and eight weeks after initiation of administration.

<Results>

Figure 2:
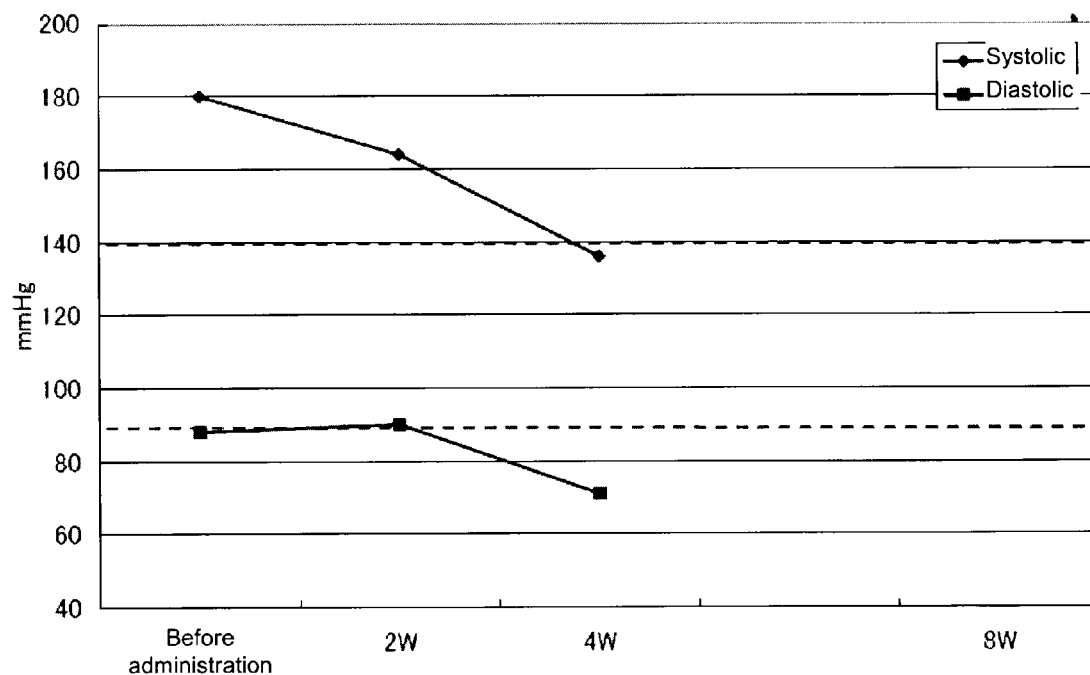
FIG. 2 shows changes in blood pressure of a hypertensive patient with a systolic blood pressure of 140 mmHg or higher.
Figure 3:
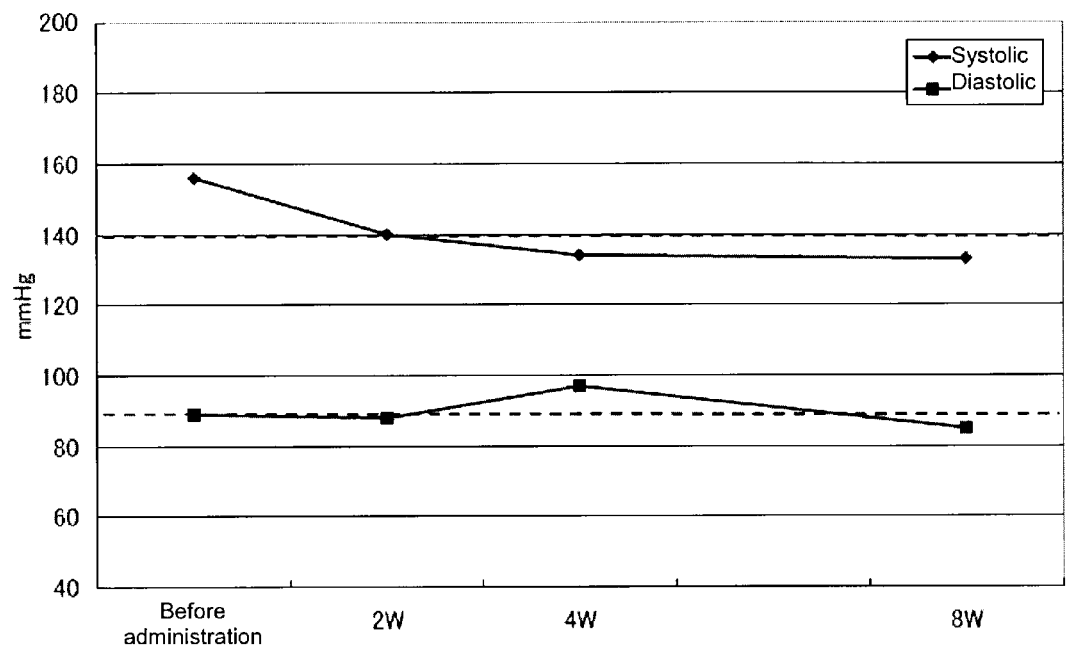
FIG. 3 shows changes in blood pressure of a hypertensive patient with a systolic blood pressure of 140 mmHg or higher.
Figure 4:
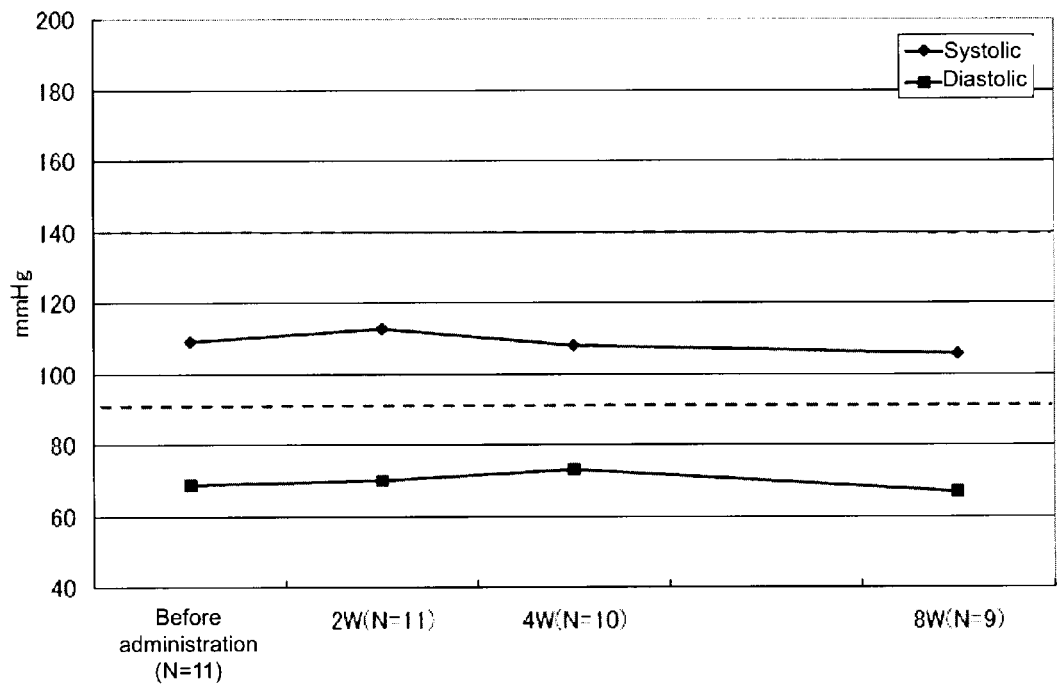
FIG. 4 shows changes in blood pressure of normotensive subjects with a systolic blood pressure of lower than 140 mmHg.

Four of all the breast cancer patients (15 patients) were defined as hypertensive; i.e., a systolic (maximum) blood pressure of 140 mmHg or higher, or a diastolic (minimum) blood pressure of 90 mmHg or higher, as measured before administration on the day of initiation of administration. In all the four hypertensive patients, systolic or diastolic blood pressure was reduced to fall within a normal pressure range two to four weeks after initiation of administration of TAS-108 (see FIGS. 1 to 3). Particularly, in a typical hypertensive patient (FIG. 2), systolic blood pressure was reduced by about 40 mmHg (i.e., from 180 mmHg to 138 mmHg) four weeks after initiation of administration of TAS-108; i.e., TAS-108 exhibited potent hypotensive effect. Meanwhile, in the remaining 11 breast cancer patients with a normal blood pressure as measured on the day of initiation of administration, no considerable change in blood pressure was observed during the course of administration of TAS-108 (see FIG. 4).

As has been shown, women undergo great change in blood pressure, lipid metabolism, bone metabolism, etc., which are closely associated with cardiovascular lesions, at their menopause as a turning point. According to the above-obtained data, TAS-108 selectively improves the blood pressure variation of postmenopausal hypertensive patients, and does not affect the blood pressure of patients with a normal blood pressure, which indicates that TAS-108 is expected to exhibit, through daily administration, an excellent therapeutic effect in hypertensive patients; in particular, postmenopausal hypertensive patients.

Example 2

<Method>

TAS-108 (100 mg) was administered to nine-week-old spontaneously hypertensive rats (SHRs) once a day for consecutive seven days. Before final administration of the test drug, and 30 minutes, one hour, two hours, and four hours after the final administration, blood pressure was measured in a state where heart rate is constant by means of an invasive automatic rat/mouse blood pressure measuring apparatus (BP-97A, product of Softron) according to the tail-cuff method (J. Lab. Clin. Med. 1971; 78: 957-962). For comparison, a solvent (0.5% HPMC) or raloxifene, serving as a control drug, was administered in a dose of 100 mg once a day for consecutive seven days.

<Results>

Figure 5:
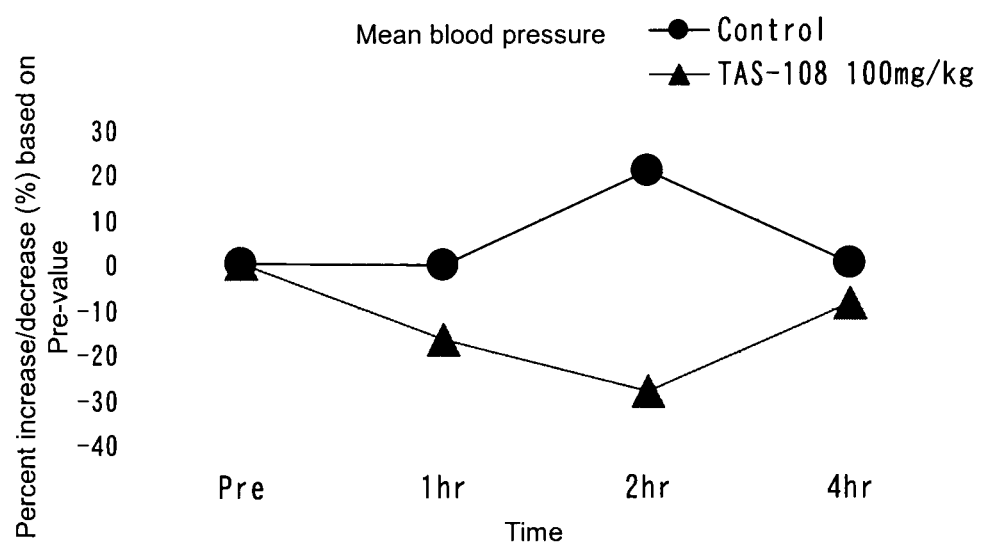
FIG. 5 shows changes in mean blood pressure through administration of TAS-108.
Figure 6:
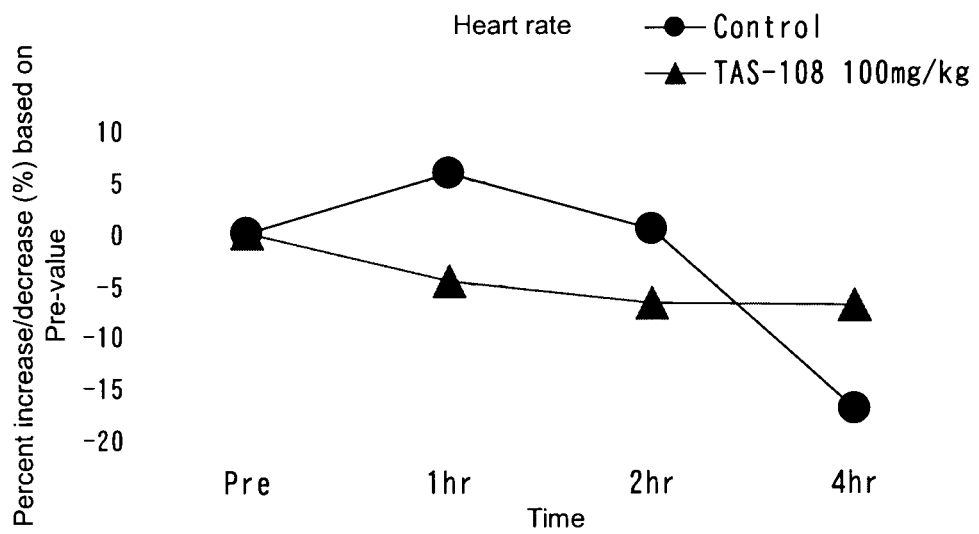
FIG. 6 shows changes in heart rate through administration of TAS-108.
Figure 7:
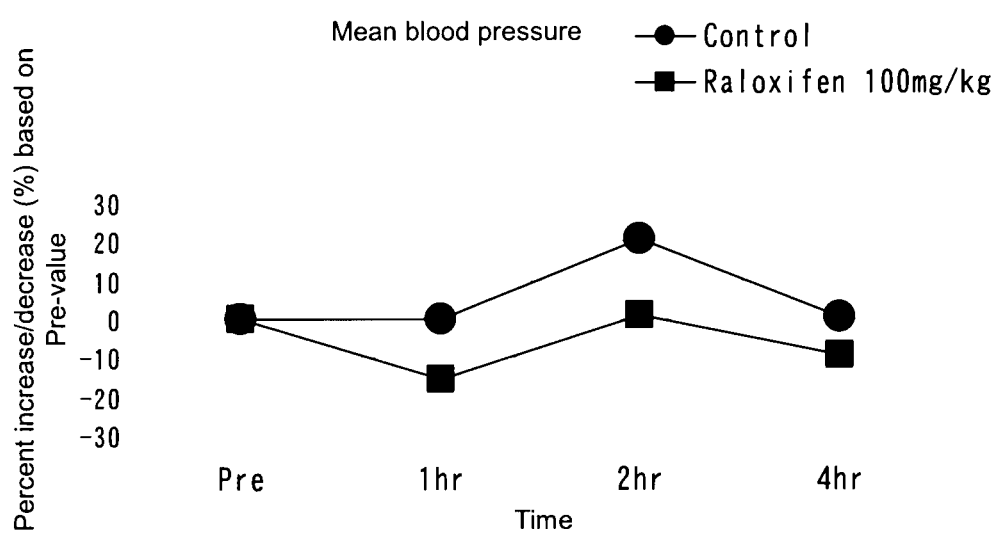
FIG. 7 shows changes in mean blood pressure through administration of raloxifene.

Percent increase/decrease in blood pressure after final administration of the test drug was obtained on the basis of the blood pressure as measured before final administration of the drug, and the thus-obtained values were compared with one another. In all the rats to which TAS-108 (100 mg) was administered, blood pressure was reduced one to two hours after administration of the drug. Specifically, mean blood pressure was reduced by 28.6%, and diastolic blood pressure was reduced by 46.9%, and percent decrease in blood pressure was maximum two hours after administration (FIG. 5). No considerable change in heart rate was observed during the course of administration (FIG. 6). Meanwhile, when the solvent or raloxifene was administered in a dose of 100 mg, no considerable change in systolic blood pressure, mean blood pressure, diastolic blood pressure, or heart rate was observed during the course of measurement (FIG. 7).

Hypertension is considered a risk factor for, for example, cardiac disease, stroke, or diabetic nephropathy, and various therapeutic drugs for hypertension have been developed (Can. J. Cardiol. 2006; 22 (7): 565-571, Can. J. Cardiol. 2006; 22 (7): 583-593). Hitherto developed and used typical hypertension therapeutic drugs include a calcium antagonist such as nifedipine, an angiotensin-converting enzyme inhibitor, and an angiotensin receptor inhibitor. Drugs exhibiting potent hypotensive effect (e.g., nifedipine) are known to pose a risk to patients through side effects causing reflex tachycardia. Therefore, attempts have been made to prepare such a hypotensive drug into a sustained-release product, or to develop a drug which does not exhibit rapid hypotensive effect and controls blood pressure in a gradual and sustained manner (Clin. Exp. Hypertens. A. 1984; 6 (8): 1485-1497, Blood Press Suppl. 1998; 1: 5-8).

According to the above-obtained data, TAS-108 exhibits potent hypotensive effect in spontaneously hypertensive rats, which are a model of essential hypertension, but does not cause reflex tachycardia (i.e., a side effect); TAS-108 exhibits hypotensive effect characterized by a decrease in diastolic blood pressure; and raloxifene (i.e., a typical SERM) does not exhibit hypotensive effect, which indicates that, unlike the case of conventional SERMs, TAS-108 is expected to exhibit, through daily administration, an excellent therapeutic effect on hypertension.

The invention claimed is:

1. A method for treatment of systemic hypertension, comprising the step of administering to a person in need thereof an effective amount of (7α)-21-[4-[(diethylamino)methyl]-2-methoxyphenoxy]-7-methyl-19-norpregna-1,3,5(10)-trien-3-ol, represented by formula (1):

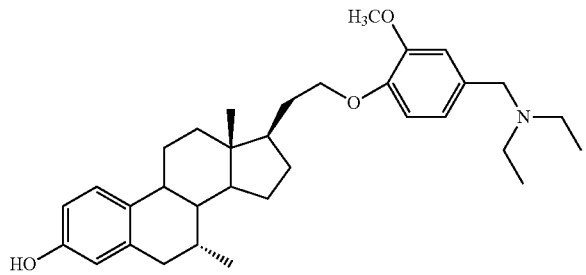 [SMILES: CCN(CC)Cc1ccc(OCC[C@H]2CCC3C4C(CC[C@@]32C)c2ccc(O)cc2C[C@H]4C)c(OC)c1]

or a pharmaceutically acceptable salt thereof.

2. The method of claim 1 further comprising the step of determining that the person has systemic hypertension.

3. The method of claim 1 further comprising the step detecting a resultant reduction in the systemic hypertension.

4. The method of claim 1 further comprising the step of determining that the person has systemic hypertension, and the step detecting a resultant reduction in the systemic hypertension.

5. The method of claim 1, wherein the person is a postmenopausal woman.

6. The method of claim 2, wherein the person is a postmenopausal woman.

7. The method of claim 3, wherein the person is a postmenopausal woman.

8. The method of claim 4 wherein the person is a postmenopausal woman.

9. The method of claim 1 wherein the person is a postmenopausal woman with breast cancer.

10. The method of claim 4 wherein the person is a postmenopausal woman with breast cancer.

11. A method for alleviating systemic hypertension, comprising the step of administering to a person with systemic hypertension (7α)-21-[4-[(diethylamino)methyl]-2-methoxyphenoxy]-7-methyl-19-norpregna-1,3,5(10)-trien-3-ol, represented by formula (1):

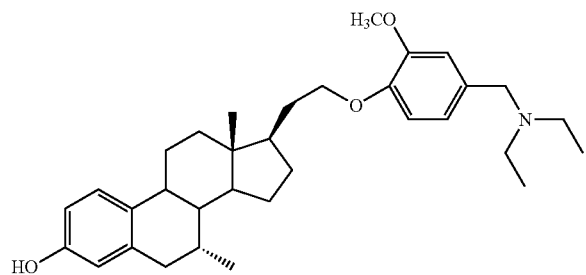 [SMILES: CCN(CC)Cc1ccc(OCC[C@H]2CCC3C4C(CC[C@@]32C)c2ccc(O)cc2C[C@H]4C)c(OC)c1]

or a pharmaceutically acceptable salt thereof.

12. The method of claim 11 further comprising the step of determining that the person has systemic hypertension.

13. The method of claim 11 further comprising the step detecting a resultant reduction in the systemic hypertension.

14. The method of claim 11 further comprising the step of determining that the person has systemic hypertension, and the step detecting a resultant reduction in the systemic hypertension.

15. The method of claim 11 wherein the person is a postmenopausal woman.

16. The method of claim 12 wherein the person is a postmenopausal woman.

17. The method of claim 13 wherein the person is a postmenopausal woman.

18. The method of claim 14 wherein the person is a postmenopausal woman.

19. The method of claim 11 wherein the person is a postmenopausal woman with breast cancer.

20. The method of claim 14 wherein the person is a postmenopausal woman with breast cancer.

* * * * *